United States Patent [19]

Kasai et al.

[11] Patent Number: 4,682,703
[45] Date of Patent: Jul. 28, 1987

[54] STOPPER FOR MEDICAL CONTAINER

[75] Inventors: Masaaki Kasai, Fuji; Kenji Ishikawa, Tokyo, both of Japan

[73] Assignee: Terumo Kabushiki Kaisha, Tokyo, Japan

[21] Appl. No.: 855,342

[22] Filed: Apr. 24, 1986

[30] Foreign Application Priority Data

Apr. 25, 1985 [JP] Japan ................................ 60-87622

[51] Int. Cl.4 ............................................ B65D 39/00
[52] U.S. Cl. .................................... 215/247; 215/364
[58] Field of Search ................ 215/247, 248, 249, 364

[56] References Cited

U.S. PATENT DOCUMENTS 3,136,440 6/1964 Krug et al. ........................... 215/247
4,444,330 4/1984 Kasai et al. .......................... 215/247

Primary Examiner—Donald F. Norton
Attorney, Agent, or Firm—Burns, Doane, Swecker & Mathis

[57] ABSTRACT

A stopper for a medical container which can tightly close an opening in said medical container and can be pierced with a syringe, which stopper is characterized by the fact that at least part of the portion thereof which possibly comes into contact with a piercing needle during the removal of said piercing needle therefrom is formed of a material containing a highly water absorbable macromolecular compound.

7 Claims, 14 Drawing Figures

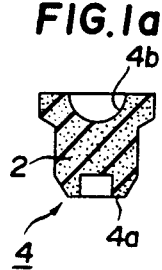
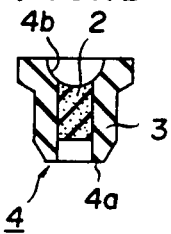
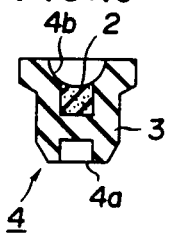
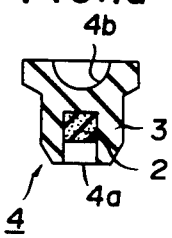
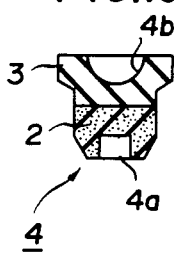
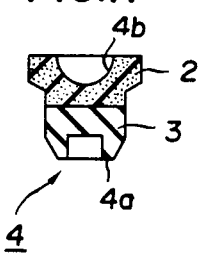
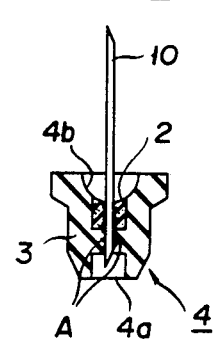
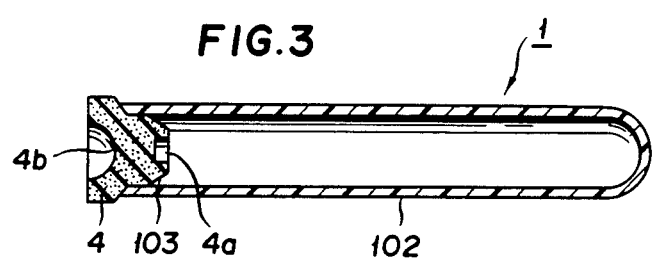
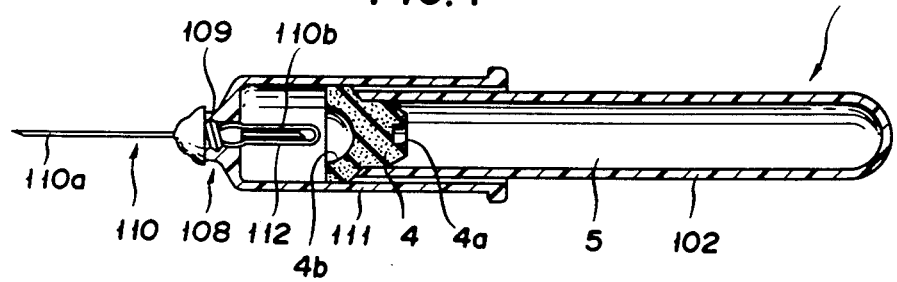

STOPPER FOR MEDICAL CONTAINER

BACKGROUND OF THE INVENTION

1. Field of the Invention

This invention relates to a stopper for a medical container. More particularly, it relates to a stopper for a medical container, which can tightly close an opening of the medical container body such as a vacuum blood collection tube and can be pierced with a needle and which can further prevent the liquid in the medical container from leaking through the puncture formed therein by piercing.

2. Description of the Prior Art

Heretofore, as the stopper for a medical container which tightly closes an opening of the medical container body such as a vacuum blood collection tube and can be pierced with a needle, the stopper made of vulcanized butyl rubber had found popular adoption because it excels in various properties such as low permeability to gas, thermal stability, and chemical resistance, possesses sufficient elasticity, and suffers only from small permanent set.

Even when the stopper of vulcanized butyl rubber which possesses sufficient elasticity and suffers only from small permanent set is used, the liquid held in the medical container inevitably leaks through the puncture formed by piercing at the time that the needle is drawn out of the stopper.

In collecting blood by a vacuum blood collection tube 101, for example, the vacuum blood collection tube 101 which is formed by tightly plugging an open end 103 of a cylindrical body 102 of the tube 101 with a stopper 104 made of vulcanized butyl rubber and sealing a prescribed gas in the cylindrical body 102 and keeping the gas under a prescribed degree of vacuum is inserted, with the open end in the lead, into a blood collection tube holder 111 which is closed at one end thereof and opened the other end thereof and has a blood collection needle 110 helically fitted into a threaded hole 109 at the closed end 108 as illustrated in FIG. 6. This blood collection needle 110 comprises a blood vessel piercing part 110a and a stopper piercing part 110b, with the stopper piercing part 110b sheathed with a rubber tip 112. Then, the blood vessel piercing part 110a of the blood collection needle 110 is thrust into the blood vessel such as, for example, the vein and the vacuum blood collection tube 101 is inserted with pressure into the closed part 108 of the blood collection tube holder 111. As the result, the stopper piercing part 110b of the blood collection needle 110 pierces the rubber tip 112 and the stopper 104 and the leading end of the part 110b reaches an inner space 105 of the blood collection tube 101. Owing to the negative pressure inside the inner space 105, the blood in the blood vessel flows into the inner space 105 of the blood collection tube 101 to an extent equalling the degree of vacuum involved. Subsequently, the vacuum blood collection tube 101 is removed from within the blood collection holder 111. Finally, the blood vessel piercing part 110a of the blood collection tube 110 is removed from the blood vessel to complete the collection of blood. Then, when the vacuum blood collection tube 101 is removed from within the blood collection tube holder 111, the blood collection needle 110 which has pierced the stopper 104 and reached the interior of the vacuum blood collection tube 101 is pulled out of the vacuum blood collection tube 101. At this time, as the blood collection needle 110 is pulled out, portion of the blood held inside the blood collection tube 101 passes through the puncture formed in the stopper 104, spills on an upper surface 104b of the stopper 104, and forms a pool of blood 114 on the upper surface 104b as shown in FIG. 8. It is inferred that this leakage is caused because the blood collection needle 110 draws in the blood at the time that it is pulled out. Besides, the possibility that the interior of the blood collection tube 101, on completion of the collection of blood, will assume a positive pressure equalling the venous pressure is considered to be another cause for the leakage.

The fact that the liquid held inside the medical container is suffered to leak and adhere to the outer side of the stopper is nothing to be desired because it has the possibility that a worker engaging in clinical test, on accidentally touching the medical container, will be polluted with the liquid adhering to the outer side of the stopper.

This invention, therefore, aims to eliminate the problems encountered by the conventional stopper for the medical container as described above.

To be specific, an object of this invention is to provide an improved stopper for a medical container.

Another object of this invention is to provide a stopper for a medical container which can tightly close an opening of the medical container and can be pierced with a syringe and which has no possibility of leakage of the liquid from the medical container through the puncture formed therein by piercing.

A further object of this invention is to provide a stopper suitable for plugging a vacuum blood collection tube.

SUMMARY OF THE INVENTION

The objects described above are accomplished by a stopper for a medical container which can tightly close an opening of the medical container and can be pierced with a needle, which stopper is characterized by the fact that at least part of the portion of the stopper which can contact the piercing needle during the extraction of the needle therefrom is formed of a material containing a highly water absorbable macromolecular compound.

This invention also discloses a stopper for a medical container, wherein the portion formed of the material containing the highly water absorbable macromolecular compound is not exposed on the inner side of the medical container. This invention further discloses a stopper for a medical container, wherein the material containing the highly water absorbable macromolecular compound containing 2 to 30% by weight of the highly water absorbable macromolecular compound. This invention further discloses a stopper for a medical container, wherein the highly water absorbable macromolecular compound can be swelled by absorbing water of an amount 50 to 10,000 times its own weight. This invention further discloses a stopper for a medical container, wherein the highly water absorbable macromolecular compound is a polyacrylamide type compound or a polyacrylate type compound. This invention further discloses a stopper for a medical container, wherein the stopper has an outside diameter smaller than the outside diameter of the medical container body.

BRIEF DESCRIPTION OF THE DRAWINGS

FIGS. 1a–1f are longitudinal cross sections of typical stoppers for a medical container as embodiments of the present invention, FIG. 2 is a longitudinal cross section illustrating a piercing needle thrust through the stopper of FIG. 1c, FIGS. 3–5 are longitudinal cross sections illustrating the stopper of the present invention as used for a vacuum blood collection tube.

DESCRIPTION OF PREFERRED EMBODIMENT

Figure 5:
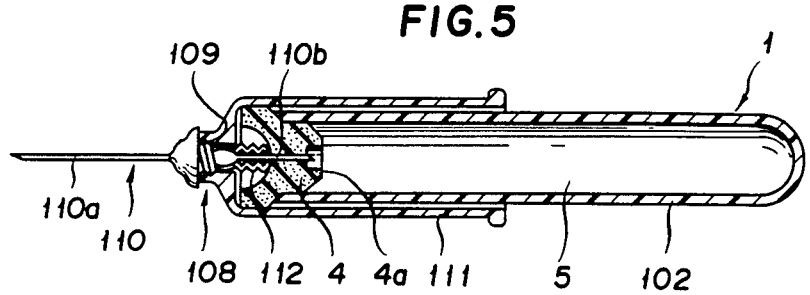
Figure 6:
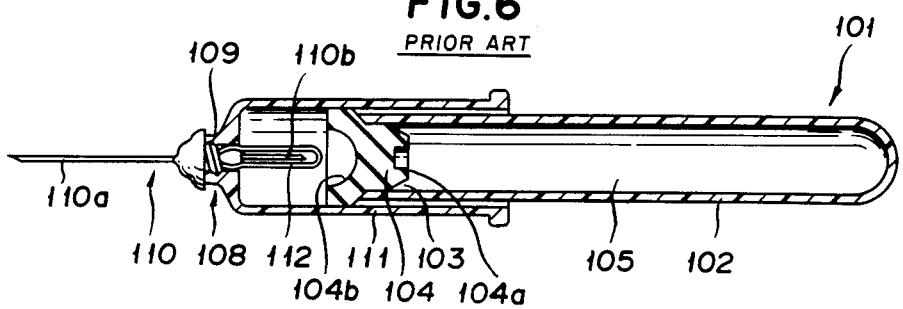
FIGS. 6–8 are longitudinal cross sections illustrating the conventional stopper as used for a vacuum blood collection tube.
Figure 8:
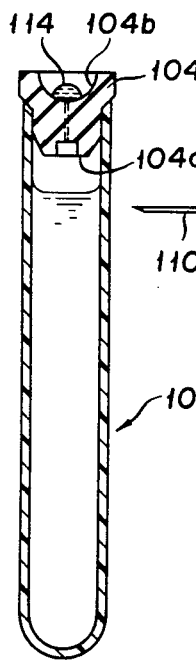
Figure 7:
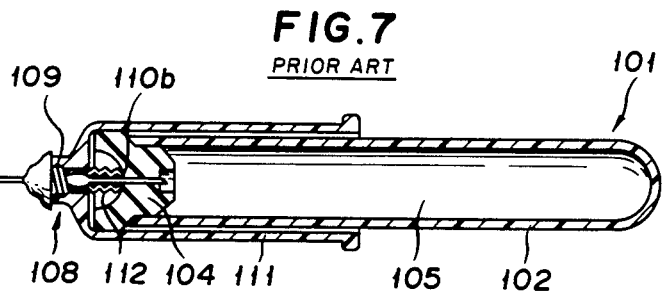

Now, the present invention will be specifically described below with reference to the accompanying drawings. FIGS. 1a–1f are diagrams showing in longitudinal cross section typical stoppers as embodiments of the present invention.

As illustrated in FIGS. 1a–1f, a stopper 4 of this invention for a medical container is constructed so that at least part of the portion thereof which possibly contacts the piercing needle during the removal thereof, namely at least part of the portion A which remains in contact with a piercing needle 10 while the piercing needle 10 is kept thrust in as illustrated in FIG. 2, is formed of a material 2 containing a highly water absorbable macromolecular compound. The size of the portion formed of the aforementioned material 2 containing a highly water absorbable macromolecular compound is not specifically defined so long as it covers part of the aforementioned portion A. For example, this portion may cover the whole of the stopper 4 as illustrated in FIG. 1a, only the central part of the stopper 4 as illustrated in FIG. 1b, only the central upper half part of the stopper 4 as illustrated in FIG. 1c, only the central lower half part of the stopper 4 as illustrated in FIG. 1d, only the lower half part of the stopper 4 as illustrated in FIG. 1e, only the upper half part of the stopper 4 as illustrated in FIG. 1f, or any other part. Desirably, a lower surface part 4a of the stopper 4, namely the portion of the stopper 4 which is exposed on the inner side of the medical container when the stopper 4 is fitted in the opening of the medical container body is not formed of the material 2 containing a highly water absorbable macromolecular compound. This is because the lower surface part 4a has the possibility of readily coming into contact with the liquid in the medical container and, if formed of the material 2, absorbing the liquid unnecessarily.

The material 2 containing a highly water absorbable macromolecular compound and used for forming part of the stopper of this invention for a medical container is a synthetic resin type or natural or synthetic rubber type compound containing a highly water absorbable macromolecular compound. Desirably, it is a synthetic resin type or natural or synthetic rubber compound containing 2 to 30% by weight, preferably 5 to 20% by weight, of a macromolecular compound.

As the highly water absorbable macromolecular compound to be contained in the aforementioned compound, any of the macromolecular compounds well known as possessing a structure obtained by slightly cross-linking and insolubilizing a water-soluble macromolecular compound can be used.

The water absorbable macromolecular compounds are modified cellulose type, modified starch type, cellulose-acryl graft type, starch-acryl graft type, plyacrylamide type and polyoxyethylene type, and polyvinyl pyrrolidone, polyvinyl alcohol, and other similar non-ionic types, plystyrene sulfonic acid, poly-2-acrylamide-2-methyl-sulfonic acid, ply-2-acrylamide-2-methylpropane sulfonic acid, and other similar plysulfonic acid types. Among other water absorbing macromolecular compounds enumerated above, those of polyacrylamide type and polyacrylate type prove particularly desirable.

The plyacrylamide type and plyacrylate type highly water absorbable macromolecular compounds include those which are obtained by aqueous solution polymerization of monomer mixtures comprising at least one water-soluble monomer such as, for example, acrylic acid, methacrylic acid, an alkali metal salt thereof or an ammonium salt thereof, acrylamide, methacrylamide, acrylonitrile, 2-hydroxyethyl acrylate, 2-hydroxyethyl methacrylate, methyl acrylate, methyl methacrylate, or maleic acid and at least one cross-linking monomer such as, for example, a diacrylate or a dimethacrylate of ethylene glycol, diethylene glycol, triethylene glycol, propylene glycol, 1,4-butane diol, 1,5-pentane diol, 1,6-hexane diol, neopentyl glycol, trimethylol propane and pentaerythritol; a triacrylate or a trimethacrylate of trimethylol propane and pentaerythritol; a tetraacrylate or a tetramethacrylate of pentaerythritol; N,N'-methylene-bis-acrylamide; N,N'-mehylene-bis-methacrylamide; or triallyl isocyanurate, those which are obtained by self-crosslinking reverse-phase suspension or emulsion plymerization of a metal salt of acrylic acid as a water-soluble monomer under the optimum conditions of neutrality, concentration, and polymerization temperature, and those which are obtained by preparing water-soluble polymers by the aforementioned polymerization of water-soluble monomers and post-crosslinking the water-soluble polymers by a physical action such as radiation or by a chemical resin, or other similar methylol group-containing compound, bisoxazoline compound, epichlorohydrin, 1,3-dichloroisopropanol, or glycerol diglycidyl ether. Among other polyacrylamide type and polyacrylate type highly water absorbable macromolecular compounds enumerated above, those obtained by the reverse-phase suspension or emulsion polyerization of alkali metal salts of acrylic acid and methacrylic acid and those obtained by the post-crosslinking with radiation prove particularly desirable.

As the synthetic resin type or natural or synthetic rubber type compound which contains the highly water absorbable macromolecular compound described above, various compounds are conceivable. Desirable synthetic resin type compounds are styrene-butadiene-styrene thermoplastic elastomers possessing elastomeric properties and other similar compounds generally passing as thermoplastic elastomers. A typical example of natural or synthetic rubber type compounds is vulcanized butyl rubber. The composite so produced may further incorporate therein a filler, a stabilizer, or a thermoplastic resin. A composite of a thermoplastic elastomer, polyisobutylene, and a partially cross-linked butyl rubber is one example. Particularly when the portion formed of the material 2 containing the highly water absorbable macromolecular compound covers the entire stopper 4 as illustrated in FIG. 1a, the material 2 is naturally required to fulfil the properties generally expected of a stopper for a medical container, such as ample elasticity enough for preventing the stopper from producing a slackened area along the contact line between the piercing needle and the stopper when the stopper is pierced with the piercing needle, sufficiently low permeability to a gas, and small susceptibility to permanent set. In this respect, vulvanized butyl rubber and thermoplastic elastomer-polyisobutylene-partially crosslinked butyl rubber composite prove particularly desirable among other composites described above.

The highly water absorbable macromolecular compound can be easily blended into the synthetic resin type or natural or synthetic rubber type compound by the use of a Henschel mixer or a Banbury mixer. The method to be used for the molding of the composite is not specifically limited. Press molding or injection molding can be effectively used for the molding. Particularly when the portion to be formed of the material 2 which contains the highly water absorbable macromolecular compound covers only part of the stopper 4 as illustrated in FIGS. 1b-1f, the molding can be effected by the insert molding or dual-color injection molding technique.

When the portio to be formed of the material 2 containing the highly water absorbable macromolecular compound covers only part of the stopper 4 as illustrated in FIGS. 1b-1f, the material 3 which forms the other portion of the stopper 4 is the same as the material forming any ordinary stopper for a medical container. This material 3 is desired to be vulcanized butyl rubber or a thermoplastic elastomer-polyisobutylene-partially crosslinked butyl rubber composite.

Now, the specific function of the stopper 4 of the present invention for a medical container will be described below with reference to the application of the stopper to a vacuum blood collection tube.

First, a vacuum blood collection tube 1 obtained by tightly plugging an open end 103 of a cylindrical body 102 for the vacuum blood collection tube with a stopper 4 of the present invention for a medical container, sealing a prescribed gas in the cylindrical body 102 of the vacuum blood collection tube, and kekeping the sealed gas under a prescribed degree of vacuum is prepared. When the vacuum blood collection tube 1 is put to tube for the collection of blood, this vacuum blood collection tube 1 is inserted, with the open end 103 in the lead, into a blood collection tube holder 111 which is opened at one end thereof and closed at the other end thereof and has a blood collection needle 110 helically fitted into a threaded hole 109 of the closed end 108 as illustrated in FIG. 4. This blood collection needle 110 consists of a blood vessel piercing part 110a and a stopper piercing part 110b, with the stopper piercing part 110b enveloped with a rubber tip 112. Then the blood vessel piercing part 110a of the blood collection needle 110 is thrust into the blood vessel such as, for example, the veins and the vacuum blood collection tube 1 is inserted under pressure into the closed part of the blood collection tube holder 111. As the result, the stopper piercing part 110b of the blood collection needle 110 pierces the rubber tip 112 and the stopper 4 and the leading end of the needle 110 reaches the inner space 5 of the blood collection tube 1 as illustrated in FIG. 5. Owing to the negative pressure in the inner space 5, the blood in the blood vessel flows into the inner space 5 of the blood collection tube 1 to an extent equalling the degree of vacuum. Then, the vacuum blood collection tube 1 is removed from within the blood collection tube holder 111. Finally, the blood vessel piercing part 110a of the blood collection tube 110 is removed from the blood vessel to complete the collection of blood. When the vacuum blood collection tube 1 is removed from within the blood collection tube holder 111, the blood collection needle 110 which has pierced the stopper 4 and reached the interior of the vacuum blood collection tube 1. In this case, part of the blood held inside the blood collection tube 1 tends to pass through the puncture formed in the stopper 4 and spill on the upper surface 4b of the stopper 4 as the blood collection needle 110 is pulled out. Since the portion formed of the material 2 containing the highly water absorbable macromolecular compound is present at least in part of the pierced part of the stopper 4 of the present invention, the blood which has entered the interior of the stopper 4 comes into contact with the highly water absorbable macromolecular compound contained in the material 2 during its passage through the portion formed of the material 2 and, consequently, caught by absorption. Thus, the part of the blood cannot leak through the puncture, spill on the upper surface 4b of the stopper 4, and form a pool of blood.

Figure 9:
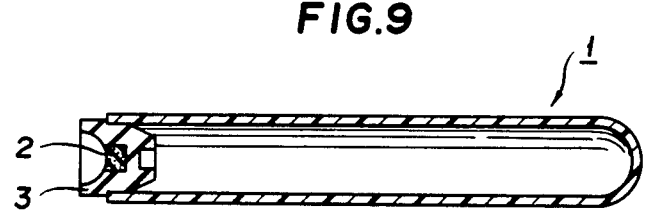
FIG. 9 is a longitudinal cross section of another typical stopper embodying the present invention in a state of actual use.

When the outside diameter of the stopper for the medical container is smaller than the outside diameter of the medical container body as illustrated in FIG. 9, the possibility of the stopper departing from the medical container body is precluded by the friction generated between the outer wall of the stopper and the inner wall of the holder during the removal of the container body.

Now, the present invention will be described more specifically below with reference to working examples.

EXAMPLE 1

A vacuum blood collection stopper was obtained by press vulcanizing a composition shown in Table 1 under ordinary vulcanizing conditions and punching the resulting vulcanized composition in the shape illustrated in FIG. 1a. A vacuum blood collection tube was produced by combining this stopper with a cylindrical body of glass for a vacuum blood collection tube. With this vacuum blood collection tube, blood was collected from the veins of a human subject by the ordinary procedure. During the collection of blood, the upper surface of the stopper was kept under observation to determine presence or absence of blood pool thereon. The results are shown in Table 6. The rating was carried out on the scale of the diameter of blood pool formed on the stopper after completion of the blood collection. The results are reported as averages of numerical values obtained of 10 samples.

TABLE 1

| | |
|---|---|
| Butyl rubber (IIR) | 80 parts by weight |
| Ethylene-propylene type copolymer (EPT) | 20 parts by weight |
| Sulfur | 0.9 part by weight |
| Zinc white | 3 parts by weight |
| Vulcanization accelerator (TL) | 0.2 part by weight |
| Zinc dibutyl dithiocarbamate (BZ) | 1.5 parts by weight |
| Kaolin clay | 50 parts by weight |
| Highly water absorbable macromolecular compound (polyacrylate type, KP-6200, made by Kao Kabushiki Kaisha) | 10 parts by weight |

CONTROL 1

As compared, a stopper was prepared by following the procedure of Example 1, except that the highly water absorbable macromolecular compound was absent from the mixture of the composition of Table 1.

With this vacuum collection tube produced by using above-stopper, blood was collected from the veins of a human subject. During the collection of blood, the upper surface of the stopper was kept under observation to determine presence or absence of blood pool thereon. The results are shown in Table 6.

EXAMPLE 2

A mixing of the composition of Table 2 was kneaded in a Banbury mixer at 150° C. and then rolled into a sheet, and subsequently pelletized. The pellets were injection molded in the shape of a rubber stopper to afford a stopper for a vacuum blood collection tube as illustrated in FIG. 1a. A vacuum blood collection tube was produced similarly to Example 1 by using this stopper and tested for leakage of blood by detection of blood pool. The results are shown in Table 6.

TABLE 2

| | |
|---|---|
| Polyisobutylene | 35 parts by weight |
| Partially cross-linked butyl rubber | 30 parts by weight |
| 1,2-Polybutadiene | 25 parts by weight |
| Mica | 25 parts by weight |
| Talc | 10 parts by weight |
| Silicone oil | 1 part by weight |
| Liquid paraffin | 2 parts by weight |
| Antioxidant | 0.05 part by weight |
| Highly water absorbable macromolecular compound (polyacrylate type, KP-6200, made by Kao Kabushiki Kaisha) | 10 parts by weight |

CONTROL 2

A stopper was prepared by following the procedure of Example 2, except that the highly water absorbable macromolecular compound was absent from the mixture of the composition of Table 2. This stopper was tested and evaluated similarly. The results are shown in Table 6.

EXAMPLE 3

From material A of the composition shown in Table 3 and Material B of the composition shown in Table 4, pellets were prepared by following the procedure of Example 2. First, the portion corresponding to the symbol 3 in the diagram of FIG. 1c was formed by injection molding the pellets of Material A. Then, the portion corresponding to the symbol 2 in the diagram of FIG. 1c was formed by insert injection molding the pellets of Material B. Consequently, a vacuum blood collection tube shaped as shown in FIG. 1c was obtained. A vacuum blood collection tube was produced by following the procedure of Example 1, using the stopper. This vacuum blood collection tube was tested and evaluated by detection of blood pool. The results are shown in Table 6.

TABLE 3

| | |
|---|---|
| Polyisobutylene | 35 parts by weight |
| Partially cross-linked butyl rubber | 30 parts by weight |
| 1,2-Polybutadiene | 25 parts by weight |
| Mica | 25 parts by weight |
| Talc | 10 parts by weight |
| Silicone oil | 1 part by weight |
| Liquid paraffin | 2 parts by weight |
| Antioxidant | 0.05 part by weight |

TABLE 4

| | |
|---|---|
| Styrene-butadiene-styrene thermoplastic elastomer (SBS) | 100 parts by weight |
| Highly water absorbable macromolecular compound (polyacrylate type, KP-6200, made by Kao Kabushiki Kaisha) | 10 parts by weight |

CONTROL 3

A stopper was prepared by following the procedure of Example 3, except that the Material B of Table 4 excluded the highly water absorbable macromolecular compound and consisted solely of SBS. The test and evaluation were carried out similarly. The results are shown in Table 6.

EXAMPLE 4

Pellets were obtained from Material A of the composition shown in Table 5 and Material B of the composition of Table 4 by following the procedures of Examples 2 and 3. Then, vacuum blood collection stoppers were obtained from the pellets by following the procedure of Example 3. The stoppers were irradiated with 2 Mrads of the gamma ray from a $^{60}$Co source for improvemnt of physical properties. A vacuum blood collection tube was prepared by following the procedure of Example 1, using the stopper. It was tested and evaluated by detection of blood pool. The results are shown in Table 6.

CONTROL 4

A stopper was prepared by following the procedure of Example 4, except that the Material B of Table 4 excluded the highly water absorbable macromolecular compound and consisted solely of SBS. The test and evaluation were carried out similarly. The results are shown in Table 6.

TABLE 5

| | |
|---|---|
| Partially cross-linked butyl rubber | 65 parts by weight |
| Polypropylene | 10 parts by weight |
| Styrene-butadiene-styrene type copolymer | 15 parts by weight |
| Mica | 35 parts by weight |
| Antioxidant | 0.05 part by weight |

TABLE 6

| | Diameter of blood pool (mm) |
|---|---|
| Example 1 | 0.5 |
| Example 2 | 2.0 |
| Example 3 | 0 (none) |
| Example 4 | 0 (none) |
| Control 1 | 3.0 |
| Control 2 | 6.0 |
| Control 3 | 1.5 |
| Control 4 | 1.0 |

As described above, this invention concerns a stopper for a medical container which can tightly close an opening in the medical container and can be pierced with a syringe and which is characterized by the fact that at least part of the portion of the stopper which can come into contact with the piercing needle during the removal of the piercing needle is formed of a material containing a highly water absorbable macromolecular compound. When the piercing needle is thrust in and pulled out of the stopper, there is no possibility of the liquid held in the medical container leaking through the puncture formed by the piercing. Thus, the possibility that the liquid in the medical container will leak and adhere to the outer side of the stopper and pollute the worker engaging in the clinical test. Thus, it is a highly satisfactory stopper for a medical container, particularly for a vacuum blood collection tube. When the portion of the stopper formed of the material containing the highly water absorbable macromolecular compound is not exposed on the inner side of the medical container, the possibility of the liquid held in the medical container being absorbed by the portion unnecessarily is precluded. The stopper of this particular structure, therefore, proves particularly suitable for a medical container. When the material containing the highly water absorbable macromolecular compound is a synthetic resin type or natural or synthetic rubber type compound containing 2 to 30% by weight of a highly water absorbable macromolecular compound, when the highly water absorbable macromolecular compound is capable of being swelled by absorbing water in an amount 50 to 10,000 times its own weight, or when the highly water absorbable macromolecular compound is of a polyacrylamide type or polyacrylate type, the effect mentioned above is manifested to still better advantage.

What is claimed is:

1. A stopper for a medical container which can be pierced with a needle, which stopper is characterized by at least part of the portion of the stopper which comes into contact with a piercing needle during the removal of said piercing needle therefrom is formed of a material containing a highly water absorbable macromolecular compound.

2. A stopper according to claim 1, wherein said stopper is constructed so that said portion formed of said material containing a highly water absorbable macromolecular compound does not contact the contents of medical container when said stopper is placed into and tightly closes the opening of a medical container.

3. A stopper according to claim 1, wherein said material containing a highly water absorbable macromolecular compound is a synthetic resin type or natural or synthetic rubber type compound containing 2 to 30% by weight of said highly water absorbable macromolecular compound.

4. A stopper according to claim 3, wherein said highly water absorbable macromolecular compound can be swelled by absorbing water in an amount 50 to 10,000 times its own weight.

5. A stopper according to claim 4, wherein said highly water absorbable macromolecular compound is of a polyacrylamide type or polyacrylate type.

6. An evacuated blood collecting device comprising a cylindrical body having one end thereof closed and the other end opened and a stopper member puncturable by a piercing needle, said stopper member serving to close tightly the open end of the cylindrical body, wherein a space formed by said cylindrical body and said stopper member is maintained under reduced pressure, which said device is characterized in that at least part of a portion of said stopper member which comes into contact with said piercing needle during the removal of said piercing needle from the stopper member is formed of a material containing a highly water absorbable macromolecular compound.

7. The evacuated blood collecting device of claim 6 wherein the stopper member has an outside diameter smaller than the outside diameter of the cylindrical body.

* * * * *